US012016958B2

(12) United States Patent
Wu et al.

(10) Patent No.: US 12,016,958 B2
(45) Date of Patent: *Jun. 25, 2024

(54) METHOD FOR DELIVERING AN AGENT TO POSTERIOR SEGMENT OF AN EYE AND USES THEREOF

(71) Applicant: NANO TARGETING & THERAPY BIOPHARMA INC., Taipei (TW)

(72) Inventors: Cheng-Hsun Wu, Zhubei (TW); Si-Han Wu, Taoyuan (TW); Yi-Ping Chen, Keelung (TW); Rong-Lin Zhang, Ligang Township (TW); Tien-Chun Yang, New Taipei (TW); Chung-Yuan Mou, Taipei (TW); Hardy Wai Hong Chan, New Taipei (TW)

(73) Assignee: NANO TARGETING & THERAPY BIOPHARMA INC., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/681,121

(22) Filed: Feb. 25, 2022

(65) Prior Publication Data

US 2022/0273583 A1    Sep. 1, 2022

Related U.S. Application Data

(60) Provisional application No. 63/154,091, filed on Feb. 26, 2021.

(51) Int. Cl.
*A61K 9/51*    (2006.01)
*A61K 9/00*    (2006.01)
*A61P 27/02*   (2006.01)
*B82Y 30/00*   (2011.01)

(52) U.S. Cl.
CPC .......... *A61K 9/5192* (2013.01); *A61K 9/0048* (2013.01); *A61P 27/02* (2018.01); *B82Y 30/00* (2013.01)

(58) Field of Classification Search
CPC ..... A61K 9/5192; A61K 9/0048; A61P 27/02; B82Y 30/00
See application file for complete search history.

(56) References Cited

U.S. PATENT DOCUMENTS

| 8,945,602 B2 | 2/2015 | Freeman | |
| 2014/0309610 A1 | 10/2014 | Canham | |
| 2019/0247228 A1* | 8/2019 | Peyman | ............... A61K 9/0051 |
| 2021/0015757 A1* | 1/2021 | Chan | ................... A61K 9/5192 |

FOREIGN PATENT DOCUMENTS

| CN | 111110636 A | 5/2020 |
| EP | 3501508 A1 * | 6/2019 |

OTHER PUBLICATIONS

Jian-Guo Sun, et al, Mesoporous Silica Nanoparticles as a Delivery System for Improving Antiangiogenic Therapy, 14 Intl. J Nanomed. 1489 (Year: 2019).*
Office Action in EP Application No. 22158988.0, dated Jun. 6, 2023, in 6 pages.
Extended European Search Report and written opinion in EP Application No. 22158988.0, dated Jul. 29, 2022, in 8 pages.
Paiva, Mayara Rodrigues Brandao et al: "Surface functionalized mesoporous silica nanoparticles for intravitreal application of tacrolimus.", XP002807034, Database accession No. NLM33290123, Database Medline [Online] US National Library of Medicine (NLM), Bethesda, MD, US; Mar. 2021 (Mar. 2021), the whole document , 2 pages.
Paiva, Mayara Rodrigues Brandao et al: "Surface functionalized mesoporous silica nanoparticles for intravitreal application of tacrolimus.", Journal of Biomaterials Applications Mar. 2021, vol. 35, No. 8, Mar. 2021 (Mar. 2021), pp. 1019-1033, ISSN: 1530-8022.

* cited by examiner

*Primary Examiner* — Sean M Basquill
(74) *Attorney, Agent, or Firm* — LADAS & PARRY LLP

(57) ABSTRACT

The disclosure provides a method for delivering an agent to posterior segment of an eye comprising administrating a pharmaceutical composition comprising the agent and mesoporous silica nanoparticles to the eye. An eye drop and a method for treating an ocular disease in a subject in need of such treatment are also provided.

16 Claims, 6 Drawing Sheets

METHOD FOR DELIVERING AN AGENT TO POSTERIOR SEGMENT OF AN EYE AND USES THEREOF

FIELD OF THE DISCLOSURE

This disclosure relates to a treating method, more specifically, the present disclosure provides a method for delivering an agent to posterior segment of an eye.

BACKGROUND OF THE DISCLOSURE

The leading causes of vision impairments and blindness are posterior segment-related diseases including Leber Hereditary Optic Neuropathy (LHON), age-related macular degeneration (AMD), diabetic macular edema, glaucoma, hereditary retinal degenerations etc. However, static and dynamic barriers of eyes, like blood-ocular barriers, refrain most of therapeutic drugs from being transported into the eye, especially to the posterior-segment of eye, resulting in insufficient drug concentrations and duration, and usually lead to the failure of clinical trials for ophthalmic drug developments.

Intravitreal drug delivery has become the gold standard for the treatment of many retinal diseases, including AMD, diabetic retinopathy, and retinal vein occlusion but each injection entails a risk of endophthalmitis, uveitis, vitreous hemorrhage and other complications. Consequently, in the place of frequent repeated intravitreal injections that are impractical for the treatment of chronic eye diseases, there is a need for an alternative means of drug delivery capable of reducing the dosing frequency no matter whether the APIs are small molecule drugs or protein (antibody) drugs.

The use of topical administration (eye drop) for the treatment of anterior segment diseases is a preferred and convenient treatment option of patients, however, eye drop administration is rarely used for treating posterior segment diseases due to its failure to deliver a sufficient amount of drugs to the retinal tissues. Blood-ocular barriers limit drug penetration and distribution, resulting in significantly low bioavailability (1-5%) and ocular penetration (less than 0.001%) in the intraocular tissues. Therefore, there is virtually no topical formulation approved by the FDA to treat posterior segment diseases.

SUMMARY OF THE DISCLOSURE

The disclosure provides a method for delivering an agent to posterior segment of an eye comprising administrating a pharmaceutical composition comprising the agent and mesoporous silica nanoparticles (MSN) to the eye.

In one embodiment of the disclosure, the agent is a small molecule drug or a biomolecule. Preferably, the small molecule drug is hydrophobic or hydrophilic. In another aspect, preferably, the biomolecule is a polypeptide, an antibody, a fragment of antibody, a fusion protein, a ligand, a biomolecule-binding protein, a functional fragment of protein, an enzyme, or a nucleotide.

Examples of the agent include, but are not limited to difluprednate, loteprednol, dexamethasone, dexamethasone sodium phosphate, fluocinolone acetonide, fluorometholone, triamcinolone, triamcinolone acetonide, rimexolone, prednisolone, medrysone, verteporfin, bevacizumab, ranibizumab, pegaptanib, aflibercept, brolucizumab, faricimab, axitinib, idebenone, azathioprine, methotrexate, mycophenolate mofetil, cyclosporine, tacrolimus, sirolimus, cyclophosphamide, chlorambucil, infliximab, adalimumab, etanercept, and brimonidine.

In some embodiments of the disclosure, the agent is loaded within pores of the mesoporous silica nanoparticles.

In some embodiments of the disclosure, the agent is linked to or adsorbed on the mesoporous silica nanoparticles through a chemical binding. Examples of the chemical binding include but are not limited to a covalent bonding, electrostatic interaction, hydrogen bonding or van der Waals force.

In some embodiments of the disclosure, the agent and the mesoporous silica nanoparticles is conjugated via a functional group or a linker.

In one embodiment of the disclosure, the method comprises administrating the pharmaceutical composition through topical administration or intravitreal, subretinal, subconjunctival, peribulbar, retrobulbar, intracameral, sub-tenon, posterior juxta scleral, or suprachoroidal injection.

In one embodiment of the disclosure, the pharmaceutical composition is in a form of an eye drop.

In one embodiment of the disclosure, the method is for delivering the agent through cornea, corneal epithelium, Bowman's layer, stroma, Descemet's membrane, corneal endothelium, conjunctiva, blood aqueous barrier, blood retinal barrier, retina, retina vessels, or retinal pigment epithelium.

In one embodiment of the disclosure, the method is for delivering the agent to layers of retina of the eye.

In one embodiment of the disclosure, the method is for delivering the agent to choroid of the eye.

In one embodiment of the disclosure, the method is for delivering the agent to sclera of the eye.

In one embodiment of the disclosure, an average particle size of mesoporous silica nanoparticles is 20 nm to 100 nm, 20 nm to 80 nm, 20 nm to 60 nm, 20 nm to 50 nm, 20 nm to 40 nm, 20 nm to 30 nm, 22 nm to 28 nm, 24 nm to 26 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured by transmission electron microscope (TEM).

In one embodiment of the disclosure, an average particle size of mesoporous silica nanoparticles used in an eye drop is 20 nm to 50 nm, 20 nm to 40 nm, 20 nm to 30 nm, 22 nm to 28 nm, 24 nm to 26 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured by transmission electron microscope (TEM).

In one embodiment of the disclosure, an average hydrodynamic diameter of mesoporous silica nanoparticles is 20 nm to 100 nm, 20 nm to 80 nm, 20 nm to 60 nm, 20 nm to 50 nm, 20 nm to 40 nm, 20 nm to 30 nm, 22 nm to 28 nm, 24 nm to 26 nm, 22 nm to 58 nm, 24 nm to 56 nm, 26 nm to 54 nm, 28 nm to 52 nm, 30 nm to 50 nm, 32 nm to 50 nm, 34 nm to 50 nm, 36 nm to 50 nm, 38 nm to 48 nm, 40 nm to 46 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured in phosphate buffered saline (PBS) by dynamic light scattering.

In one embodiment of the disclosure, an average hydrodynamic diameter of mesoporous silica nanoparticles used in an eye drop is 20 nm to 60 nm, 20 nm to 50 nm, 20 nm to 40 nm, 20 nm to 30 nm, 22 nm to 28 nm, 24 nm to 26 nm, 22 nm to 58 nm, 24 nm to 56 nm, 26 nm to 54 nm, 28 nm to 52 nm, 30 nm to 50 nm, 32 nm to 50 nm, 34 nm to 50 nm, 36 nm to 50 nm, 38 nm to 48 nm, 40 nm to 46 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured in phosphate buffered saline (PBS) by dynamic light scattering.

In one embodiment of the disclosure, the mesoporous silica nanoparticles are with or without metal atoms. In one further embodiment of the disclosure, the mesoporous silica nanoparticles are free of metal atoms.

The present disclosure provides an eye drop comprising a pharmaceutical composition, the pharmaceutical composition comprising agent and mesoporous silica nanoparticles, wherein the agent is loaded by mesoporous silica nanoparticles; wherein an average particle size of the mesoporous silica nanoparticles is 20 nm to 50 nm measured by transmission electron microscope, or an average hydrodynamic diameter of the mesoporous silica nanoparticles or an average hydrodynamic diameter of the mesoporous silica nanoparticles loaded with the agent is less than 60 nm measured in phosphate buffered saline (PBS) by dynamic light scattering.

The present disclosure also provides a method for treating an ocular disease in a subject in need of such treatment comprising the method for delivering the agent to posterior segment of the eye.

In some embodiments of the disclosure, the ocular disease is a posterior segment-related disease.

In one embodiment of the disclosure, the ocular disease is correlated to abnormal reactive oxygen species level, abnormal apoptosis, mitochondrial dysfunctions, inflammation, abnormal protein level, or protein misfolding/aggregation/decrease in or complete loss of function.

In one embodiment of the disclosure, treatment of the ocular disease is through treating a tissue of an eye.

In one embodiment of the disclosure, the tissue of the eye is retina, choroid, sclera, macula, fovea, optic nerve, vitreous humor, iris, cornea, pupil, lens, zonule fibers, or ciliary muscle.

In one embodiment of the disclosure, treatment of the ocular disease is through treating a cell of an eye.

In one embodiment of the disclosure, the cell of the eye is muller cells, photoreceptors, bipolar cells, ganglion cells, horizontal cells, or amacrine cells.

In one embodiment of the disclosure, treatment of the ocular disease is through treating a nerve cell.

In one embodiment of the disclosure, the nerve cell is a photoreceptor, bipolar cell, ganglion cell, horizontal cell, or amacrine cell.

In one embodiment of the disclosure, the ocular disease is age-related macular degeneration, Leber hereditary optic neuropathy, glaucoma, X-linked juvenile retinoschisis (XLRS), diabetic retinopathy, diabetic macular edema, retinal vein occlusion, uveitis, and endophthalmitis, myopic foveoschisis, macular edema, enhanced blue cone syndrome, inflammation following cataract surgery (Irvine-Gass syndrome), retinal detachment, cystoid macular edema, retinal tear, and retinal injury.

In one embodiment of the disclosure, the ocular disease correlated to abnormal reactive oxygen species level is selected from the group consisting of Leber's hereditary optic neuropathy, age-related macular degeneration, cataract, diabetic retinopathy (DR), glaucoma, dry eye, uveitis, and retinitis pigmentosa.

In one embodiment of the disclosure, the ocular disease correlated to abnormal angiogenesis is selected from the group consisting of wet age-related macular degeneration (AMD), diabetic retinopathy, retinal artery or vein occlusion, retinopathy of prematurity (ROP), neovascular glaucoma, and corneal neovascularization secondary to infectious or inflammatory processes.

In one embodiment of the disclosure, the ocular disease correlated to abnormal apoptosis is selected from the group consisting of Leber's hereditary optic neuropathy, glaucoma, retinitis pigmentosa, cataract formation, retinoblastoma, retinal ischemia, and diabetic retinopathy.

In one embodiment of the disclosure, the ocular disease correlated to mitochondrial dysfunctions is selected from the group consisting of Leber's hereditary optic neuropathy, age-related macular degeneration, diabetic retinopathy, glaucoma, Kearns-Sayre syndrome (KSS), and dominant optic atrophy (DOA).

In one embodiment of the disclosure, the ocular disease correlated to inflammation is selected from the group consisting of uveitis, orbital inflammatory disease, scleritis, episcleritis, iritis, sarcoidosis, Fuchs' heterochromic iridocyclitis, pemphigoid, ocular toxoplasmosis and ocular graft versus host disease, and dry eye.

In one embodiment of the disclosure, the ocular disease correlated to abnormal protein level or protein misfolding/aggregation/decrease in or complete loss of function is selected from the group consisting of cataract, age-related macular degeneration, retinitis pigmentosa (RP), X-linked Juvenile Retinoschisis (XLRS), and Stargardt's disease.

The present disclosure is described in detail in the following sections. Other characteristics, purposes and advantages of the present disclosure can be found in the detailed description and claims.

BRIEF DESCRIPTIONS OF THE DRAWINGS

DETAILED DESCRIPTION OF THE DISCLOSURE

Figure 1:
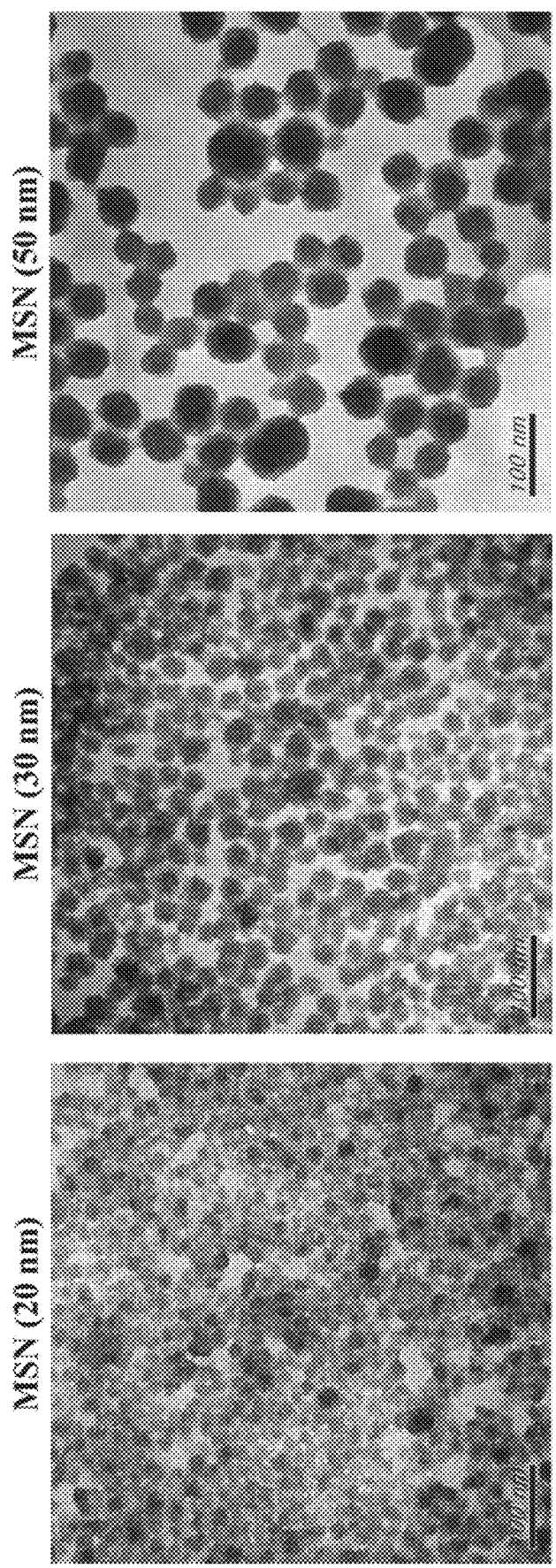
FIG. 1 shows the TEM images of internal and outer surface modified MSNs with different sizes.

The present disclosure can be more readily understood by reference to the following detailed description of various embodiments of the disclosure, the examples, and the chemical drawings and tables with their relevant descriptions. It is to be understood that unless otherwise specifically indicated by the claims, the disclosure is not limited to specific preparation methods, carriers or formulations, or to particular modes of formulating the compound of the disclosure into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

In the present disclosure, unless particularly specified, the prefix "nano-" as used herein means a size of about 300 nm or less. Unless particularly specified, the prefix "meso-" as used herein, unlike the definition suggested by IUPAC, means a size of about 5 nm or less.

In the present disclosure, the term "silane" as used herein refers to derivatives of $SiH_4$. Normally, at least one of the four hydrogens is replaced with substituents such as alkyl, alkoxyl, amino, etc., as described below. The term "alkoxysilane" as used herein refers to a silane having at least one alkoxyl substituent directly bonded to the silicon atom. The term "organo-alkoxysilane" as used herein refers to a silane having at least one alkoxyl substituent and at least one hydrocarbyl substituent directly bonded to the silicon atom. The term "silicate source" as used herein refers to substances which can be deemed as a salt form or an ester form of orthosilicic acid, for example sodium orthosilicate, sodium metasilicate, tetraethyl orthosilicate (tetraethoxysilane, TEOS), tetramethylorthosilicate, or tetrapropylorthosilicate. Optionally, the hydrocarbyl substituent can be further substituted or interrupted with a heteroatom.

In the present disclosure, the term "hydrocarbyl" as used herein refers to a monovalent radical derived from hydrocarbons. The term "hydrocarbon" as used herein refers to a molecule that consists of carbon and hydrogen atoms only. Examples of the hydrocarbons include, but are not limited to, (cyclo)alkanes, (cyclo)alkenes, alkadienes, aromatics, etc. When the hydrocarbyl is further substituted as mentioned above, the substituent can be halogens, amino groups, a hydroxy group, a thiol group, etc. When the hydrocarbyl is interrupted with a heteroatom as mentioned above, the heteroatom can be S, O or N. In the present disclosure, a hydrocarbyl preferably comprises 1 to 30 C atoms.

In the present disclosure, the term "alkyl" refers to a saturated, straight or branched alkyl, which comprises preferably 1-30 carbon atoms, and more preferably 1-20 carbon atoms. Examples of alkyl include, but are not limited to, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or the like.

In the present disclosure, the term "alkylene" refers to a divalent radical of an alkyl as noted above. The term "short chain" represents that the radical or repeating unit contains at most 6 carbon atoms in the main chain, preferably at most 4 carbon atoms.

In the present disclosure, the term "alkoxyl" or "alkoxy" as used herein means a group having a formula "—O-alkyl," wherein the definition of the "alkyl" in said formula has the meaning of "alkyl" as stated above.

In the present disclosure, the term "cycloalkyl" as used herein means a saturated or partially unsaturated cyclic carbon radical containing 3 to 10 ring carbon atoms and more preferably 3 to 8 ring carbon atoms, and optionally an alkyl substituent(s) on the ring. Examples of cycloalkyl include, but are not limited to, cyclopropyl, cyclopropenyl, cyclobutyl, cyclopentyl, cyclohexyl, 2-cyclohexen-1-yl, and the like.

In the present disclosure, the term "halogen" or "halo" denotes fluorine, chlorine, bromine or iodine.

In the present disclosure, the term "amino" as used herein means a functional group of the formula $—NR_1R_2$, wherein $R_1$ and $R_2$ each independently represent hydrogen or a hydrocarbyl group as defined above.

In the present disclosure, the expression "internal surface" refers to the surface of the "wall" defining the pore, and the expression "outer surface" refers to the surface of the outermost layer, wall or structure of the nanoparticles.

In the present disclosure, the term "agent" as used herein refers to a substance having a therapeutic effect in an organism, particularly in an eye. The agent as disclosed herein may be a small molecule drug. The small molecule drug, such as an active pharmaceutical ingredient (API), may be hydrophobic or hydrophilic; in another aspect, the small molecule drug may carry positive charge, negative charge, or may be neutral. In a particulate example, the agent is axitinib, dexamethasone, and dexamethasone sodium phosphate. The agent as disclosed herein may be a biomolecule. Examples of the biomolecule include, but are not limited to a polypeptide, an antibody, a fragment of antibody, a fusion protein, a ligand, a biomolecule-binding protein, a functional fragment of protein, an enzyme, or a nucleotide.

In some embodiments of the disclosure, the agent is an ocular drug. Examples of the agent include, but are not limited to, a steroid such as difluprednate, loteprednol, dexamethasone, dexamethasone sodium phosphate, fluocinolone acetonide, fluorometholone, triamcinolone, triamcinolone acetonide, rimexolone, prednisolone, medrysone; a vascular endothelial growth factor (VEGF) inhibitor, such as verteporfin, bevacizumab, ranibizumab, pegaptanib, aflibercept, brolucizumab, faricimab; a VEGF receptor inhibitor, such as axitinib; a drug for LHON, such as idebenone; an immunosuppressor such as azathioprine, methotrexate, mycophenolate mofetil, cyclosporine, tacrolimus, sirolimus, cyclophosphamide, chlorambucil; an TNF alpha inhibitor such as infliximab, adalimumab, etanercept; and other ocular drugs such as brimonidine.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a liquid solution, a suspension, an emulsion, a granule, an ampoule, an injection, an implant, an insert, an infusion, a kit, an ointment, a lotion, a liniment, a cream, a gel, a spray, a drop, an aerosol, or a combination thereof for topical administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The disclosure provides a method for delivering an agent to posterior segment of an eye comprising administrating a pharmaceutical composition comprising the agent and mesoporous silica nanoparticles to the eye.

The present disclosure provides an eye drop comprising a pharmaceutical composition, the pharmaceutical composition comprising agent and mesoporous silica nanoparticles loaded within pores of the mesoporous silica nanoparticles; wherein an average particle size of the mesoporous silica nanoparticles is less than 50 nm, preferably from 20 nm to 50 nm measured by transmission electron microscope, or an average hydrodynamic diameter of the mesoporous silica nanoparticles or an average hydrodynamic diameter of the mesoporous silica nanoparticles loaded with the agent is less than 60 nm measured in phosphate buffered saline (PBS) by dynamic light scattering.

The present disclosure also provides a method for treating an ocular disease in a subject in need of such treatment comprising the method for delivering the agent to posterior segment of the eye.

With certain surface modifications, MSNs may have potential in providing the desired pharmacological effect, such as delivering an agent to posterior segment of an eye. Various MSNs can be used in this disclosure for loading drugs. In some embodiments, MSNs are modified with a variety of surface functional groups to improve their biocompatibility and design for different purposes. For example, the MSNs having surface modification with (i) an organic molecule, oligomer or polymer and optionally (ii) a positively charged molecule, a negatively charged molecule, oligomer or polymer, and pore internal surface modification with a terminal hydrocarbyl moiety, a positively charged molecule, or a negatively charged molecule.

Examples of the organic molecule, oligomer or polymer (i) include, but are not limited to, short-chain poly(alkylene glycol) (PAG), e.g., poly(ethylene glycol) (PEG), poly(propylene glycol) (PPG), PEG-PPG copolymers, etc. Further (organic) modifying agent(s) can be introduced to modify the properties of MSNs (e.g., surface properties, etc.), and examples thereof include, but are not limited to, propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl)ethylenediaminetriacetic acid (EDTAS), (3-trihydroxysilyl)propyl methylphosphonate (THPMP), methyltriacetoxysilane(MTAS), (3-mercaptopropyl)trimethoxysilane (MPTMS), zwitterionic silane, etc.

Examples of the positively charged molecule, oligomer or polymer (ii) include, but are not limited to, polyethylenimine (PEI); alkoxylsilane-terminated (poly)alkylene(poly)amine, such as N-[3-(trimethoxysilyl)propyl]-N,N,N-trimethylammonium chloride (TA), N-[3-(Trimethoxysilyl)propyl]ethylenediamine (EDPTMS), $N^1$-(3-Trimethoxysilylpropyl)diethylenetriamine, etc.; organo-alkoxysilane such as 3-aminopropyltrimethoxysilane (APTMS), 3-aminopropyl triethoxysilane, etc. Examples of the negatively charged molecule include, but are not limited to organo-alkoxysilanes that have negatively charged in pH 7 condition.

It would be necessary to use the positively charged molecule, negatively charged molecule, oligomer or polymer (ii) having a length shorter than the organic molecule, oligomer or polymer (i) when making the surface modification, which is believed to reduce non-specific binding toward a non-target.

Examples of the terminal hydrocarbyl moiety include, but are not limited to, a terminal aromatic moiety, a terminal (cyclo)aliphatic moiety or combinations thereof. The expression "terminal" implies that the hydrocarbyl moiety is directly linked to the silicon atom of the silica nanoparticle. In some embodiments, the terminal aromatic moiety is substituted with lower alkyl, or halogen. In a further embodiment, the terminal aromatic moiety is derived from trimethoxyphenylsilane (TMPS). In some embodiments, the terminal (cyclo)aliphatic moiety comprises (cyclo)alkyl, (cyclo)alkenyl or combinations thereof, which can be optionally substituted with lower alkyl or halogen. In one embodiment, the terminal aliphatic moiety is derived from long-chain alkyl silanes with 4 to 18 carbon atoms, which include, but are not limited to, butyltrimethoxysilane, butyltriethoxysilane, hexyltrimethoxysilane, hexyltriethoxysilane, octyltrimethoxysilane, octyltriethoxysilane, iso-octyltrimethoxysilane, iso-octyltriethoxysilane, dexyltrimethoxysilane, dexyltriethoxysilane, dodexyltrimethoxysilane, dodexyltriethoxysilane, tetradecyltrimethoxysilane, tetradecyltriethoxysilane, hexadecyltrimethoxysilane, haxadecyltriethoxysilane, octadecyltrimethoxysilane, and octadecyltriethoxysilane, preferably trimethoxy $C_{6-8}$ alkylsilane.

In one embodiment, pore surface modification can be achieved by using a silane(s) having no terminal hydrocarbyl moiety and a silane(s) having at least one terminal hydrocarbyl moiety, wherein the terminal hydrocarbyl moiety comes from the silane(s) having at least one terminal hydrocarbyl moiety. In one embodiment, the amount of terminal hydrocarbyl moiety per particle, expressed by the molar ratio of the silane(s) having no terminal hydrocarbyl moiety to the silane(s) having at least one terminal hydrocarbyl moiety is at least 50:1, or at least 40:1, at least 35:1, at least 30:1, at least 25:1, at least 20:1, at least 15:1, or within any numeric ranges consisting of the endpoints noted above, e.g., from 15:1 to 50:1, from 20:1 to 40:1, etc. In one embodiment, calculation and/or measurements can be made to obtain the number of silane(s) having at least one terminal hydrocarbyl moiety per particle.

In one embodiment, pore surface modification can be achieved by using a positively charged silane, the amount of positively charged silane per particle, expressed by the molar ratio of TEOS to the positively charged silane is at least 20:1 or at least 15:1, at least 10:1, at least 5:1, or at least 3:1 or within any numeric ranges consisting of the endpoints noted above, e.g., from 3:1 to 20:1, from 5:1 to 10:1, from 6:1 to 8:1, etc.

In one embodiment, pore surface modification can be achieved by using a negatively charged silane, the amount of negatively charged silane per particle, expressed by the molar ratio of TEOS to the negatively charged silane is at least 40:1 or at least 35:1, at least 30:1, at least 25:1, at least 20:1, at least 15:1, at least 10:1 or at least 5:1 or within any numeric ranges consisting of the endpoints noted above, e.g., from 5:1 to 40:1, from 5:1 to 20:1, from 7:1 to 15:1, from 7:1 to 10:1, etc.

In one embodiment, the mesoporous silica nanoparticle of the present disclosure has an average particle size of 100 nm or less, 90 nm or less, 80 nm or less, 70 nm or less, 60 nm or less, 50 nm or less, 40 nm or less, 30 nm or less, 20 nm or less, measured by TEM. Particularly, an average particle size of mesoporous silica nanoparticles is 20 nm to 100 nm, 20 nm to 80 nm, 20 nm to 60 nm 20 nm to 50 nm, 20 nm to 40 nm, 20 nm to 30 nm, 22 nm to 28 nm, 24 nm to 26 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured by TEM.

In one embodiment of the disclosure, an average particle size of mesoporous silica nanoparticles used in an eye drop is 20 nm to 50 nm, 20 nm to 40 nm, 20 nm to 30 nm, 22 nm to 28 nm, 24 nm to 26 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured by transmission electron microscope (TEM).

In one embodiment, the mesoporous silica nanoparticle of the present disclosure has a pore size of 50 nm or less, 45 nm or less, 40 nm or less, 35 nm or less, 30 nm or less, 25 nm or less, 20 nm or less, 15 nm or less, 10 nm or less, 5 nm or less, or 3 nm or less, or any numeric ranges consisting of the endpoints noted above, such as from 1 nm to 3 nm, 3 nm to 50 nm, 5 nm to 35 nm, 10 nm to 45 nm, etc.

In one embodiment, the mesoporous silica nanoparticle of the present disclosure has an average hydrodynamic diameter of 100 nm or less, 90 nm or less, 80 nm or less, 70 nm or less, 60 nm or less, 50 nm or less, 40 nm or less, 30 nm or less measured in phosphate buffered saline by dynamic light scattering. Particularly, an average hydrodynamic diameter of mesoporous silica nanoparticles is 20 nm to 100 nm, 20 nm to 80 nm, 20 nm to 60 nm, 20 nm to 50 nm, 20 nm to 40 nm, 20 nm to 30 nm, 22 nm to 28 nm, 24 nm to 26 nm, 22 nm to 58 nm, 24 nm to 56 nm, 26 nm to 54 nm, 28 nm to 52 nm, 30 nm to 50 nm, 32 nm to 50 nm, 34 nm to 50 nm, 36 nm to 50 nm, 38 nm to 48 nm, 40 nm to 46 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured in PBS by dynamic light scattering.

In one embodiment of the disclosure, an average hydrodynamic diameter of mesoporous silica nanoparticles used in an eye drop is 20 nm to 60 nm, 20 nm to 50 nm, 20 nm to 40 nm, 20 nm to 30 nm, 22 nm to 28 nm, 24 nm to 26 nm, 22 nm to 58 nm, 24 nm to 56 nm, 26 nm to 54 nm, 28 nm to 52 nm, 30 nm to 50 nm, 32 nm to 50 nm, 34 nm to 50 nm, 36 nm to 50 nm, 38 nm to 48 nm, 40 nm to 46 nm, 22 nm to 48 nm, 24 nm to 46 nm, 26 nm to 44 nm, 28 nm to 42 nm, 30 nm to 40 nm, 32 nm to 38 nm, or 34 nm to 38 nm, measured in phosphate buffered saline (PBS) by dynamic light scattering.

In certain embodiments, the zeta potential (in pH 7.4 condition) of the MSNs may range from −30 to +30 mV, −25 to +25 mV, −20 to +20 mV, −15 to +15 mV, or −10 to +10 mV, or a reasonable numeric range within the endpoints mentioned herein, for example −30 to −10, −15 to +20 mV, −10 to +25 mV, −15 to +10 mV, +10 to +30 mV etc. In one embodiment, the mesoporous silica nanoparticle has a BET surface area of 1000 $m^2/g$ or less, 750 $m^2/g$ or less, or 500 $m^2/g$ or less.

In some embodiments of the disclosure, the mesoporous silica nanoparticle has at least one of the following characteristics:

(a) surface modification with (i) an organic molecule, oligomer or polymer and (ii) a positively charged molecule, oligomer or polymer, wherein the molar ratio of (i) and (ii) ranges from 60:1 to 2:1;
(b) pore internal surface modification with a terminal hydrocarbyl moiety;
(c) an average particle size of 60 nm or less, measured by TEM; and
(d) an average hydrodynamic diameter of 60 nm or less, measured in PBS by dynamic light scattering.

In one embodiment, the MSN has characteristics (a) and (b); preferably has characteristics (a), (b) and (c); preferably has characteristics (a), (b) and (d); and more preferably has characteristics (a), (b), (c) and (d).

MSN loading with the agent which exhibits barrier penetration capability shows advantages in being a high potential drug delivery system for treating an ocular disease. All the examples, ingredients, reaction conditions or parameters illustrated in the examples are merely for illustration purposes and are not intended to limit the material or the preparation method by the exemplary embodiments described herein.

In some embodiments of the disclosure, the agent is loaded within pores of the mesoporous silica nanoparticles.

In some embodiments of the disclosure, the agent is linked to or adsorbed on the mesoporous silica nanoparticles through a chemical binding. Examples of the chemical binding include but are not limited to a covalent bonding, electrostatic interaction, hydrogen bonding or van der Waals force.

In some embodiments of the disclosure, the agent and the mesoporous silica nanoparticles is conjugated via a functional group or a linker.

MSNs possess well-defined structures and high density of surface silanol groups which can be modified with a wide range of organic functional groups. The different sizes of MSNs are prepared using an ammonia base-catalyzed method. The particle size is controlled by adjusting ammonia concentration, amount and concentration of the silane source, and reaction temperature, etc.

In one aspect, MSNs can be prepared with the following steps: (a) providing an alkaline solution containing a surfactant at a concentration sufficient for forming micelles; (b) introducing silane source(s) into the solution; (c) introducing (i) an organic molecule, oligomer or polymer and optionally (ii) a positively charged molecule, a negatively charged molecule, oligomer or polymer into the solution; (d) conducting hydrothermal treatment to the solution; (e) collecting the products; (f) removing the residual surfactant(s) from the products; and optionally (g) purifying or cleaning the products.

Typically, 0.2 to 0.4 g of a surfactant was dissolved in 150 to 250 mL of an aqueous, alkaline solution (e.g., ammonium hydroxide solution (0.1 to 0.25M)) at the desired temperature (45 to 65° C.) in a sealed beaker. After 10 to 30 minutes of stirring and then 150 to 450 µL of a silane (TEOS) and optionally 15 to 110 µL of an internal surface modulating silane (for pore internal surface modification) in 0.8 to 1.6 mL of a solvent (e.g., alcohols, such as ethanol) were sequentially or simultaneously added to the solution under stirring, preferably vigorous stirring. After 0.5 to 1.5 hours of stirring, another addition of 100 to 300 µL of a silane (TEOS) in 0.6 to 1.3 mL of a solvent (e.g., alcohol, such as ethanol) was added. After 2 to 4 hours of the reaction, the 700 to 1200 pt of PEG-silane (a silane having PEG moiety, e.g., (2-[methoxy(polyethyleneoxy)propyl]-trimethoxysilane)) with 10 to 600 µL a charged molecule, oligomer or polymer (e.g., TA-silane, (N-[3-(trimethoxysilyl)propyl]-N,N,N-trimethylammonium chloride)) in 2.5 to 4 mL of a solvent (e.g., alcohols, such as ethanol) was introduced into the reaction. After the mixture was stirred for 0.5 to 1.5 hours, it was aged at the desired temperature (e.g., 45 to 65° C.) without stirring for at least 12 hours. Then, the solution was sealed and placed in an oven at 65 to 75° C. for 18 to 60 hours or 65 to 75° C. and 85 to 95° C. each for 20 to 28 hours of hydrothermal treatment. The as-synthesized product was washed and collected by centrifugation or cross-flow system. For removing the surfactant in the pores of the MSNs, the as-synthesized product was incubated in 40 to 60 mL of acidic solvent (e.g., alcohols, such as ethanol) containing an acid (such as hydrochloric acid (37%)) for 0.5 to 1.5 hours of extraction at 55 to 65° C., and the incubation was conducted once or several times. The products were washed and harvested by centrifugation or cross-flow system and finally stored, preferably in 85% or higher ethanol. For different pore internal surface modified MSN synthesis, different hydrocarbyl moiety, positively charged molecules and negatively charged molecules were used. For different outer surface modified MSN-PEG synthesis, different positively charged molecules, oligomers or polymers, such as TA-silane, EDPTMS-silane or other functional-silanes were used. MSN have various surface charge through modulating the ratio of PEG to charge molecules present on MSN-PEG (the surface charge can be negative charge, neutral or positive charge).

In one embodiment, the silane source comprises tetraethoxysilane (TEOS), tetramethoxysilane (TMOS), sodium silicate or a mixture thereof. Surface modifying agents can be used for adjusting the properties of MSNs. In one embodiment, the (organic) modifying agent(s) include, but are not limited to, propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl) ethylenediaminetriacetic acid (EDTAS), (3-trihydroxysilyl) propyl methylphosphonate (THPMP), methyltriacetoxysilane(MTAS), (3-mercatopropyl) trimethoxysilane (MPTMS), zwitterionic silane, etc.

Examples of surfactants suitable for preparing MSNs include, but are not limited to, cationic surfactants, anionic surfactants and non-ionic surfactants. Proper surfactants are selected based on the conditions of reaction, such as pH value, ionic strength, temperature, reactants and products, etc. Examples of cationic surfactants include, but are not limited to, pH-dependent primary, secondary, or tertiary amines with a long-chain hydrocarbyl group, and the terminal amine group bears positive charge when presenting below a specific pH value, such as primary and secondary amines becoming positively charged at pH<10, for example octenidine dihydrochloride; and permanently charged quaternary ammonium salts, e.g., cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB). Examples of anionic surfactants include, but are not limited to, sulfate, sulfonate, and phosphate salts or esters; such as ammonium lauryl sulfate, sodium lauryl sulfate (sodium dodecyl sulfate, SLS, or SDS), and the related alkyl-ether sulfates, sodium laureth sulfate (sodium lauryl ether sulfate or SLES), and sodium myreth sulfate, docusate (dioctyl sodium sulfosuccinate), perfluorooctanesulfonate (PFOS), perfluorobutanesulfonate, alkyl-aryl ether phosphates, alkyl ether phosphates, etc. Examples of non-ionic surfactants include, but are not limited to, poly(oxyethylene)nonylphenyl ether, polyoxyethylene glycol sorbitan alkyl ester, polyethylene glycol alkyl ether, glucoside alkyl ether, polyethylene glycol octylphenyl ether, polyethylene glycol alkylphenyl ether, glycerol alkyl ester, polypropylene glycol alkyl ethers, block copolymers, poloxamers, cocamide MEA, cocamide DEA, lauryldimethylamine oxide or polyethoxylated tallow amine.

The different sizes of MSNs may be prepared by using an ammonia base-catalyzed method. In one aspect, the MSNs are prepared under highly diluted and low surfactant conditions. In the present disclosure, MSNs preferably have an average diameter of less than 100 nm, measured by TEM. In the present disclosure, MSNs used in an eye drop preferably have an average diameter of less than 50 nm, measured by TEM. Control of the size of MSNs can be achieved by adjusting the ammonia concentration, amount and concentration of alkoxylsilane, reaction temperature, etc. Without being bound to the theory, when the ammonia concentration is higher, the size of MSNs may become larger and vice versa; when the amount of alkoxylsilane is larger, the size of MSNs may become larger and vice versa; In various embodiments, 0.14-0.5 g CTAB in 150 mL ammonium hydroxide solution is used, the ammonia concentration ranges from 0.05 to 1.5 M, preferably from 0.1 to 0.5 M, more preferably from 0.1 to 0.25 M; the amount of alkoxysilane added into 150 mL ammonium hydroxide solution ranges from 1 mL to 5 mL, preferably from 1 mL to 3 mL, more preferably from 2 mL to 2.5 mL of ethanolic TEOS (i.e., TEOS in ethanol, about 0.862 to 1.2 M); and the reaction temperature ranges from 30° C. to 60° C., preferably from 40° C. to 60° C., more preferably from 50° C. to 60° C.; any combination of these conditions may serve as an embodiment of the present disclosure.

At least one agent can be loaded onto and/or into MSNs, for example distributed within the space in MSNs, on the surface of MSNs, etc. The agent may be properly selected based on the size thereof and the concerned disorders/diseases.

In one embodiment of the disclosure, the mesoporous silica nanoparticles are with or without metal atoms. In one further embodiment of the disclosure, the mesoporous silica nanoparticles are free of metal atoms.

In some embodiments of the disclosure, the pharmaceutical composition comprises the agent and optionally a pharmaceutically acceptable carrier or excipient.

In some embodiments of the disclosure, the pharmaceutical composition comprises an effective amount of the agent.

For overcoming the blood-ocular barrier, the characteristics of mesoporous silica nanoparticles such as the nanoparticle size, surface charge, and constitution, etc., can be modulated to increase penetration of static and dynamic barriers of eyes, thereby improving ocular bioavailability. Mesoporous silica nanoparticles have been deemed to have great potential as drug delivery systems due to their unique physical/chemical properties, such as: large pore volume, chemical/thermal stability, high loading capacity, adjustable surface properties and excellent biocompatibility. A small size MSN (<100 nm) with particle and pore surface modification by a specific functional group and ratio is provided to encapsulate hydrophobic drug into the pore space and make the particle exhibit excellent suspension in aqueous solution. Furthermore, for ocular drug delivery, the MSN can modulate the nanoparticle size, surface charge, conjugated ligands to increase penetration of static and dynamic barriers of eyes, the barriers restrict most of therapeutic drug transported into the posterior-segment of eye. Herein, the agent is evaluated as a potential treatment of posterior segment-related ocular disease and the administration route could be intravitreal administration or in a form of an eye drop. MSNs offer an approach to conquer the problems faced by ocular drug delivery in clinical use especially for retinal disease. There is a need to deliver therapeutics via a suitable delivery system that has the potential to overcome the ocular barriers, enhance the therapeutic efficacy, reduce the administration frequency, and offer alternatives of administration route than intravitreal injections.

Eye drop is the most convenient and patient compliant route of drug administration for ocular disease, but ocular drug delivery for posterior segment related eye diseases (retinal diseases) via eye drop is one of the most challenging area. Static and dynamic barriers of eyes refrain most of therapeutic drugs from being transported into the posterior-segment of eye, resulting in low ocular penetration and bioavailability. To-date, limited approved drugs and drug candidates for treatment of posterior segment of eye diseases and there is no approved eye drops for retinal diseases as most drug molecules cannot effectively enter the posterior areas of the eye. The formulation of eye drop is highly challenging but very important for making the drug successful. Different type of nanoparticle has been developed as an eye drop formulation for retinal disease treatment (e.g. polymer/cyclodextrin nanoparticle), the particle size of the drug contained cyclodextrin nanoparticle was up to hundreds nanometer to 1 micrometer, resulting in the nanoparticle was stay long time on cornea to release the drug to penetrate into eye instead of the nanoparticle carry drug across barriers of eye into the posterior segment of eyes. In this invention, smaller hydrodynamic sizes of the drug loaded MSN can increase penetration of static and dynamic barriers of eyes and carry the therapeutic drug into the posterior-segment of eye for treating posterior segment eye diseases. MSN nanoparticles can address the unmet medical needs of eye drop formulation including making a high drug concentration aqueous solution, overcoming the barriers of eyes to enhance bioavailability, maintaining effective drug concentrations at the target site.

The agent loaded in, conjugated on, or adsorbed on MSN provides slow-release property and increase the half-life of the agent that can reduce the dosing frequency. MSN with specific tailored properties can effectively penetrate the static and dynamic barriers of eyes to deliver therapeutic agents to the posterior-segment of eyes via eye drop administration that would open up the possibility of using MSN nanoparticle to develop eye drop formulation. The agent loaded MSN solution can be a potential nano-formulation for eye drug delivery and the administration route could be topical (eye drop), intravitreal, subconjunctival, subretinal, peribulbar, posterior juxta scleral, suprachoroidal retrobulbar, intracameral, sub-tenon, systemic injection, etc.

The pharmaceutical composition according to the disclosure is preferably administrated topically by any method known in the art. The appropriate route, formulation and administration schedule can be determined by those skilled in the art. In the present disclosure, the pharmaceutical composition can be formulated in various ways, according to the corresponding route of administration, such as a liquid solution, a suspension, an emulsion, a granule, an ampoule, an injection, an implant, an insert, an infusion, a kit, an ointment, a lotion, a liniment, a cream, a gel, a spray, a drop, an aerosol, or a combination thereof. If necessary, it may be sterilized or mixed with any pharmaceutically acceptable carrier or excipient, many of which are known to one of ordinary skill in the art.

Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution. The aerosol composition may optionally contain additional formulation excipients well known in the art such as surfactants e.g. oleic acid or lecithin and cosolvents e.g. ethanol. Preferably, the pharmaceutical composition is in a form of an eye drop.

Preferably, the method comprises administrating to an eye of said subject the pharmaceutical composition through intravitreal, subretinal, subconjunctival, peribulbar, retrobulbar, intracameral, sub-tenon, posterior juxta scleral, or suprachoroidal injection. More preferably, the method comprises administrating to an eye of said subject the pharmaceutical composition through intravitreal or subretinal injection.

In one embodiment of the disclosure, the method is for delivering the agent to layers of retina of the eye. MSN modulates the distribution of particle/agent in the layers of retina including but are not limited to inner limiting membrane, nerve fiber layer, ganglion cell layer, inner plexiform layer, inner nuclear layer, outer plexiform layer, outer nuclear layer, outer limiting membrane, photoreceptor layer or retinal pigment epithelium In one embodiment of the present disclosure, it demonstrates that in vivo the smaller size MSN enter mouse retinal cells efficiently, the distribution and retention time in retina can be managed by particle size and surface properties. Therefore, MSN can be designed to deliver drug to the lesions of diseases such as the lesions of AMD, retinal degenerations, etc. are in the deeper layers of retina (PR, RPE); and the lesions of LHON, X-linked Juvenile Retinoschisis (XLRS), etc. are in the middle and upper layers of retina.

MSNs are especially amenable to all sorts of modification to adjust their porous structures, particle sizes, surface properties and degrees of pegylations, resulting in nanoparticles that can penetrate deep into the posterior segment of the eye. MSNs offer a simple nano-formulation for ocular drug delivery that can enhance solubility, deliver various drugs with diverse physicochemical properties across barriers of eyes, and enhance the therapeutic efficacy. The drug-loaded nanoparticle especially for poor aqueous solubility drugs exhibits high initial drug concentrations and good dispersion in aqueous solution without aggregation, the administration route can be eyedrops or intravitreal injection. MSNs are composed of amorphous silica which are known to be biocompatible and biodegradable. No significant acute eye irritation/corrosion and ocular toxicity for eye tissues were observed in the preliminary ocular toxicity study in rats.

In one embodiment of the disclosure, the ocular disease is correlated to abnormal reactive oxygen species level, abnormal apoptosis, mitochondrial dysfunctions, inflammation, abnormal protein level or protein misfolding/aggregation/decrease in or complete loss of function.

In one embodiment of the disclosure, the ocular disease is Leber's hereditary optic neuropathy or X-linked Juvenile Retinoschisis.

In one embodiment of the disclosure, the ocular disease correlated to abnormal reactive oxygen species level is selected from the group consisting of Leber's hereditary optic neuropathy, age-related macular degeneration (AMD), cataract, diabetic retinopathy (DR), glaucoma, dry eye, uveitis, and retinitis pigmentosa.

In one embodiment of the disclosure, the ocular disease correlated to abnormal angiogenesis is selected from the group consisting of wet age-related macular degeneration (AMD), diabetic retinopathy, retinal artery or vein occlusion, retinopathy of prematurity (ROP), neovascular glaucoma, and corneal neovascularization secondary to infectious or inflammatory processes.

In one embodiment of the disclosure, the treatment of the ocular disease is through reducing a level of reactive oxygen species.

Mitochondrion is the primary production site of reactive oxygen species (ROS) for the majority of eukaryotic cells. While not wishing to be limited by theory, it is Applicant's belief that, ROS are produced as natural byproducts of normal metabolism of oxygen in Oxidative Phosphorylation (OXPHOS) which play important roles in cell signaling and homeostasis. ROS include peroxides, superoxide, hydroxyl radical, and singlet oxygen. Their levels also increase due to environmental stress (e.g., UV or heat exposure), pollutants, tobacco, smoke, drugs, xenobiotics, radiation, etc., collectively, characterized as oxidative stress. Oxidative stress often leads to damages in proteins, lipids, and DNA, and in the case of LHON, deaths of RGCs resulting in optic neuropathy.

In one embodiment of the disclosure, the ocular disease correlated to abnormal angiogenesis is selected from the group consisting of wet age-related macular degeneration (AMD), diabetic retinopathy, retinal artery or vein occlusion, retinopathy of prematurity (ROP), neovascular glaucoma, and corneal neovascularization secondary to infectious or inflammatory processes.

Age-related macular degeneration is a leading cause of irreversible blindness in adults over 50 years old which may result in blurred or no vision in the center of the visual field. The global prevalence of AMD is approximately 8.69% among adults ages 45-85 years, the disease affects about 170 million worldwide, among that about 11 million individuals in the United States. AMD is classified into 2 types. (I) Dry AMD (no choroidal neovascularization present), patient may have yellow deposits, called drusen, in their macula. A few small drusen may not cause changes in vision but as they get bigger and more numerous, they might dim or distort the vision. As the condition gets worse, the light-sensitive cells in macula get thinner and eventually die. In the atrophic form, patients may have blind spots in the center of vision. As that gets worse, patient may lose central vision. (II) Wet AMD (CNV present) can be attributed to blood vessels grow from underneath of macula. These blood vessels leak blood and fluid into retina. The vision is distorted so that straight lines look wavy. Patient may also have blind spots and loss of central vision. These blood vessels and their bleeding eventually form a scar, leading to the permanent loss of central vision. No medical or surgical treatment is available for dry AMD. Wet AMD can be treated with VEGF inhibitors (Ranibizumab, aflibercept, and brolucizumab) and also laser coagulation therapy, unfortunately, there is no cure although treatments may slow down the disease progression and keep patients from having a severe loss of vision.

Leber Hereditary Optic Neuropathy is the most common inherited mitochondrial disorder and typically affects young males (males:females ratios as high as 9:1). The patients diagnosed with LHON may initially be asymptomatic, or experience a mild blurring of the central visual field of one eye, but symptoms may progress from mild unilateral visual loss to severe bilateral visual loss. If vision loss starts in one eye, the other eye is usually affected within several weeks or months. Over time, vision in both eyes worsens with a severe loss of sharpness and color vision.

The prevalence of LHON is around 1/50,000 people worldwide, the disease affects approximately 10,000 people in United States and can lead to legal blindness. There is no cure for LHON and supportive treatment options are also limited. Currently, it is with antioxidant supplements (idebenone [granted an orphan drug designation], vitamins B12 and C, Coenzyme-Q10, brimonidine, and lutein) to help reduce the neurotoxic stress due to reactive oxygen species have shown minimal benefit but may be recommended. In addition, gene therapy trials are currently being pursued.

In one embodiment of the disclosure, the ocular disease correlated to abnormal apoptosis is selected from the group consisting of Leber's hereditary optic neuropathy, glaucoma, retinitis pigmentosa, cataract formation, retinoblastoma, retinal ischemia, and diabetic retinopathy.

In one embodiment of the disclosure, the treatment of the ocular disease is through reducing apoptosis.

In one embodiment of the disclosure, the ocular disease correlated to mitochondrial dysfunctions is selected from the group consisting of Leber's hereditary optic neuropathy, age-related macular degeneration, diabetic retinopathy, glaucoma, Kearns-Sayre syndrome (KSS), and dominant optic atrophy (DOA).

In one embodiment of the disclosure, the treatment of the ocular disease is through treating mitochondrial dysfunctions.

Point mutations of mtDNA are strictly maternally inherited. Genetically, over 90% of LHON are caused by three mtDNA point mutations: m.3460G>A, m.11778G>A and m.14484T>C, which all involved different NADH dehydrogenase (ND) subunits of Complex I in the mitochondrial respiratory chain. Among the three, m.11778G>A mtDNA mutation within the MT-ND4 gene is the most common cause of LHON (60%). Unlike other mitochondrial disorders, whose phenotypes are often heteroplasmic, most LHON patients carry the mtDNA pathogenic mutations in a homoplasmic fashion (100% of the mtDNA molecules are mutated). Mitochondrial dysfunctions caused by reduced functions of ND Complex I caused the death of retinal ganglion cells (RGCs). While not wishing to be limited by theory, it is Applicant's belief that the loss of RGCs in LHON is due to the release of cytochrome c into the cytosol and also Fas-induced apoptosis. It may also be related to the caspase-independent apoptosis driven by energetic failures. The mitochondrial dysfunction related RGC apoptosis eventually lead to atrophic patterns.

In one embodiment of the disclosure, the ocular disease correlated to inflammation is selected from the group consisting of uveitis, orbital inflammatory disease, scleritis, episcleritis, iritis, sarcoidosis, Fuchs' heterochromic iridocyclitis, pemphigoid, ocular toxoplasmosis and ocular graft versus host disease, and dry eye.

In one embodiment of the disclosure, the ocular disease correlated to abnormal protein level or protein misfolding/aggregation/decrease in or complete loss of function is selected from the group consisting of cataract, age-related macular degeneration, retinitis pigmentosa (RP), X-linked Juvenile Retinoschisis (XLRS), and Stargardt's disease.

In one embodiment of the disclosure, treatment of the ocular disease is through treating a tissue of an eye.

In one embodiment of the disclosure, the tissue of the eye is retina, choroid, sclera, macula, fovea, optic nerve, vitreous humor, iris, cornea, pupil, lens, zonule fibers, or ciliary muscle.

In one embodiment of the disclosure, treatment of the ocular disease is through treating a cell of an eye.

In one embodiment of the disclosure, the cell of the eye is muller cells, photoreceptors, bipolar cells, ganglion cells, horizontal cells, or amacrine cells.

In one embodiment of the disclosure, treatment of the ocular disease is through treating a nerve cell.

In one embodiment of the disclosure, the nerve cell is a retinal nerve cell photoreceptor, bipolar cell, ganglion cell, horizontal cell, or amacrine cell.

The following examples are provided to aid those skilled in the art in practicing the present disclosure.

EXAMPLES

Materials, Methodologies and Test Models
Transmission Electron Microscope (TEM)
Transmission electron microscopy (TEM) is used to directly examine and verify the appearance of the silica nanoparticles. The TEM images were taken on a Hitachi H-7100 transmission electron microscope operated at an accelerated voltage of 100 kV. Samples dispersed in ethanol were dropped on carbon-coated copper grids and dried in air for TEM observation.

Dynamic Light Scattering (DLS) and Zeta Potential
Size measurements of the silica nanoparticles in different solution environments were performed with Dynamic Light Scattering (DLS) on a Malvern Zetasizer Nano ZS (Malvern, UK). The (solvated) particle sizes formed in different solutions were analyzed: $H_2O$ and PBS buffer solution (pH7.4) at room temperature. Surface charge (zeta potential) of the silica nanoparticles in PBS (0.01×, pH 7.4) at particle concentration 0.1 mg/mL were performed by a Malvern Zetasizer Nano ZS.

Elemental Analysis
The mass percentage of carbon, nitrogen, oxygen and hydrogen in silica nanoparticle was determined by elemental analyzer (elementar Vario EL cube type for NCSH, German).

Example 1

Preparation of Mesoporous Silica Nanoparticles with Various Pore Internal Surface and Outer Surface Modifications.

The outer surface or pore surface of MSN can be easily modified with various functional groups individually. The MSNs of different sizes were prepared using an ammonia base-catalyzed method under highly diluted and low surfactant conditions. The particle size was controlled by adjusting ammonia concentration, TEOS amount added, and reaction temperature. For different pore internal surface modified MSN synthesis, different hydrocarbyl moiety (such as octyltriethoxysilane (C8-silane)), positively charged molecules (such as TA-silane, EDPTMS-silane, etc.) and negatively charged molecules were used. For different outer surface modified MSN-PEG synthesis, different positively charged molecules, oligomers or polymers, such as TA-silane, EDPTMS-silane or other functional-silanes were used. Typically, 0.2 to 0.4 g of a surfactant was dissolved in 150 to 250 mL of an aqueous, alkaline solution (e.g., ammonium hydroxide solution (0.1 to 0.25M)) at the desired temperature (45 to 65° C.) in a sealed beaker. After 10 to 30 minutes of stirring and then 150 to 450 µL of a silane (TEOS) and 15 to 110 µL of an internal surface modulating silane (for pore internal surface modification) in 0.8 to 1.6 mL of a solvent (e.g., alcohols, such as ethanol) were sequentially or simultaneously added to the solution under stirring, preferably vigorous stirring. After 0.5 to 1.5 hours of stirring, another addition of 100 to 300 µL of a silane (TEOS) in 0.6 to 1.3 mL of a solvent (e.g., alcohol, such as ethanol) was added. After 2 to 4 hours of the reaction, the 700 to 1200 µL of PEG-silane (a silane having PEG moiety, e.g., (2-[methoxy(polyethyleneoxy)propyl]-trimethoxysilane)) with 10 to 600 µL a positively charged molecule, oligomer or polymer (e.g., TA-silane, (N-[3-(trimethoxysilyl)propyl]-N,N,N-trimethylammonium chloride)) in 2.5 to 4 mL of a solvent (e.g., alcohols, such as ethanol) was introduced into the reaction. After the mixture was stirred for 0.5 to 1.5 hours, it was aged at the desired temperature (e.g., 45 to 65° C.) without stirring for at least 12 hours. Then, the solution was sealed and placed in an oven at 65 to 75° C. for 18 to 60 hours or 65 to 75° C. and 85 to 95° C. each for 20 to 28 hours of hydrothermal treatment. The as-synthesized product was washed and collected by centrifugation or cross-flow system. For removing the surfactant in the pores of the MSNs, the as-synthesized product was incubated in 40 to 60 mL of acidic solvent (e.g., alcohols, such as ethanol) containing an acid (such as hydrochloric acid (37%)) for 0.5 to 1.5 hours of extraction at 55 to 65° C., and the incubation was conducted once or several times. The products were washed and harvested by centrifugation or cross-flow system and finally stored, preferably in 85% or higher ethanol. MSN have various surface charge through modulating the ratio of PEG to charge molecules present on MSN-PEG, for example, the surface charge of C8-MSN can be negative charge, neutral or positive charge through modifying different ratio of PEG to TA on the surface of C8-MSN.

Example 2

TEM and DLS Measurements

The MSNs as synthesized in Example 1 were subject to TEM and DLS measurements, all particles have small particle size and good dispersity in PBS. The results are shown in Table 1 below.

TABLE 1

| MSN type | Sample | Size (TEM) | Size (DLS) In PBS | Zeta potential |
|---|---|---|---|---|
| C8-MSN (internal surface modification with C8-silane) | NTT2_158 | 19.1 ± 2.3 nm | 44.2 nm | Neutral |
|  | NTT2_183 | 28.88 ± 6.6 nm | 43 nm | Neutral |
|  | NTT2_182 | 43.7 ± 4.8 nm | 55.5 nm | Neutral |
|  | C8-RMSN-PEG/TA(2_1) | 29.5 ± 2.44 nm | 47.2 nm | Positive 31.7 mV |
|  | C8-RMSN-PEG | 29.7 ± 2.97 | 45.9 nm | Negative −11 mV |
| PC-MSN (internal surface modification with positively charged silane) | PC-MSN | 30 ± 5 nm | 40.2 nm | positive 22 mV |
| NC-MSN (internal surface modification with positively charged silane) | NC-MSN | 25.1 ± 2.6 nm | 39.7 nm | Negative −25.3 mV |

Example 3

Small Molecule Drug Loaded in MSN

The API (small molecule) can be loaded within the pores of MSN and API can be hydrophobic or hydrophilic drugs. Encapsulation of hydrophobic and hydrophilic drugs in the MSN did not significantly affect the dispersity and hydrodynamic size in a medium (medium is biologically similar to or equivalent to phosphate buffered saline (PBS)) that is critical for retaining the surface properties and penetration capability of MSN. The smaller hydrodynamic sizes of the API loaded MSNs (API@MSN) allow for better aqueous dispersion to keep API@MSN mobile during the penetration process. Furthermore, only limited volume can be injected into the eye or instilled on the eye surface, therefore high initial drug concentrations are needed to achieve effective levels in the posterior segment considering the deficient bioavailability. MSN can increase the water solubility of the hydrophobic drug up to million-times improvement, and the drug-loaded nanoparticle still exhibits good dispersion in aqueous solution without aggregation. API @ MSN eye drop formulations facilitate better drug solubility, resulting in much higher drug concentrations in aqueous solution (0.1-2% (mg/mL)), especially for hydrophobic compounds, that solves the issue of the drug which is hardly prepared in an aqueous solution into high drug concentration for eye drop formulation.

Hydrophobic Drug Loading in Pore Internal Surface Modified MSN

The C8-MSN particle was dispersed in 50 mL of $H_2O$. The hydrophobic drug stock solution (drug was dissolved in organic solution, e.g. DMSO) was slowly dropped into the particle solution with vigorous stirring. After the solution was fully mixed, the mixture was further diluted with 50 mL of $H_2O$ for decreasing the DMSO ratio. For removing the trace amount of free drug aggregates, the mixture was filtered with 0.22 μm of filter. Next, the mixture was washed with 7 to 10-fold of $H_2O$. Finally, the product was stored in $H_2O$.

Hydrophilic Drug Loading in Pore Internal Surface Modified MSN

The PC-MSN or NC-MSN particle was dispersed in water, buffer or mixture solution with buffer and organic solution. The hydrophilic drug stock solution (drug was dissolved in water, buffer or organic solution) was slowly dropped into the particle solution with vigorous stirring and the mixture was stirred for 15 to 60 minutes. For removing the trace amount of free drug that was not loaded into MSN, the mixture was washed with 7 to 10-fold of buffer or $H_2O$. Finally, the product was stored in buffer or $H_2O$.

Axitinib (AXT) Loading in Pore Internal Surface Modified MSN

NC-MSN particle was dispersed in 0.25 mL 50% DMSO with 10 mM acetate buffer, then 18.8 μL AXT stock (25 mg/mL in DMSO) was added and mixed well. After wash, the AXT-loaded particle was stored in acetate buffer.

TABLE 2

| API@MSN | Size (DLS) In PBS | Drug-to-MSN ratio (wt %) | Drug concentration in eye drop formulation |
|---|---|---|---|
| Hydrophilic_API@MSN | <50 nm | 5~10% | 0.1-2% (mg/mL) |
| Hydrophobic_API@MSN | <50 nm | 4~8% | 0.1-1% (mg/mL) |

Protein Drugs (Antibody) Conjugated or Adsorbed on MSN

The outer surface of MSN can be modified with various functional groups to modulate the protein-MSN conjugation approach, interaction between protein and MSN, and particle properties. The protein drug can be conjugated onto the surface of MSN via a functional group or a linker or adsorbed onto the surface of MSN via interaction (electrostatic interaction, hydrogen bonding, van der Waals force, etc.) between drugs and MSN.

Properties of antibody-MSN which may be correlated to the particle distribution in the eye: particle size (TEM), hydrodynamic diameter (DLS), surface charge (positive charge, neutral, negative charge), surface modification with poly(ethylene glycol) moiety and optionally a functional group, The length/molecular weight of functional group or linker, number of protein drug conjugated or adsorbed on MSN.

Example 4

Particle Size Affects Intraocular Distribution and Kinetics (Administration Route: Intravitreal Injection)

Figure 2:
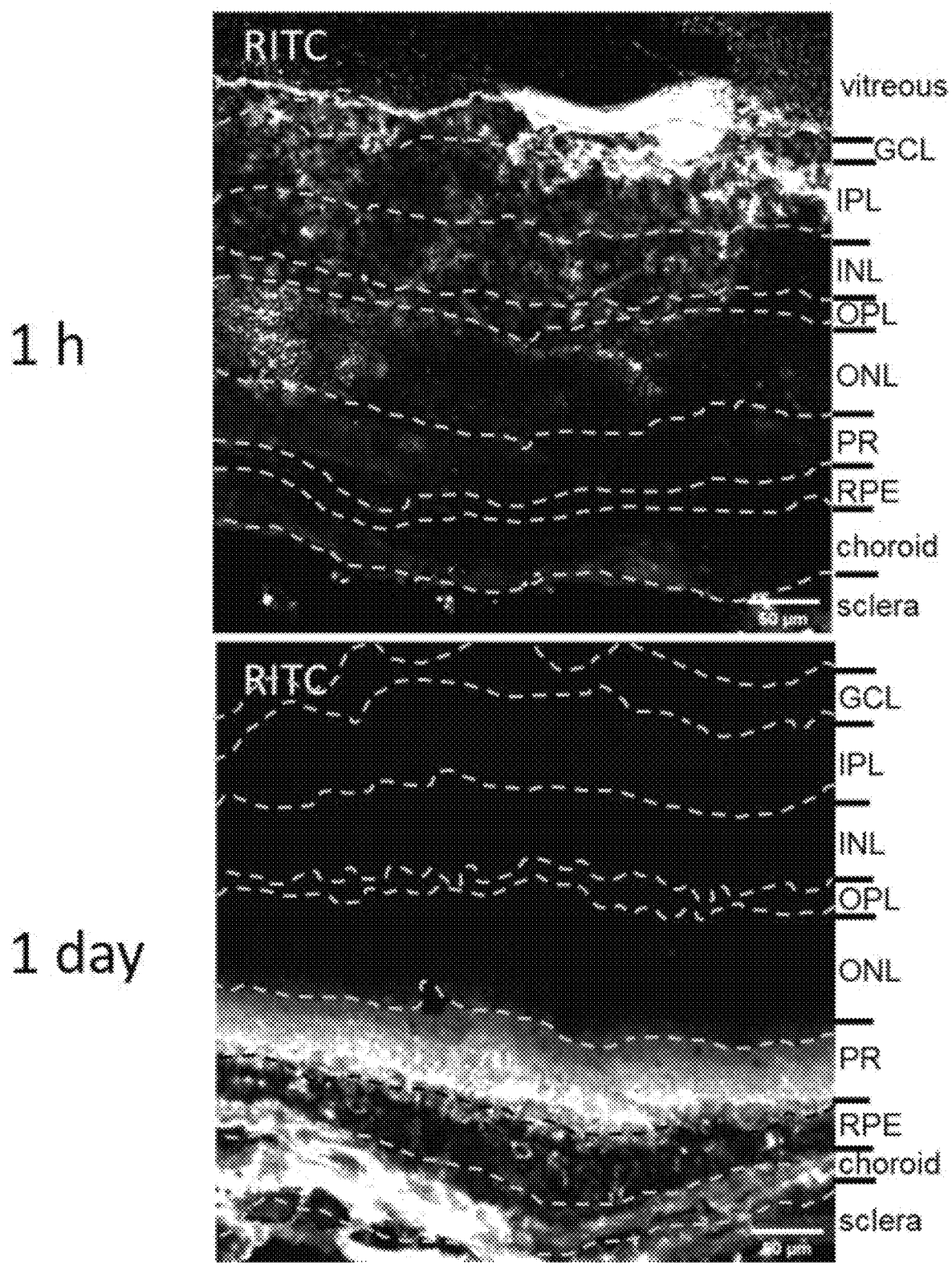
FIG. 2 shows the distribution of 30 nm MSN particles in layers of retina, choroid, and sclera 1 hour and 1 day after intravitreal injection.

Fluorescent labeled MSNs with different particle sizes (TEM size: 20, 30, and 50 nm respectively) were suspended in PBS and injected into mouse eye through intravitreal injection. 1 hour and 24 hours after injection, the eyes of the mice were harvested and the frozen section of eyes will be analyzed by immunochemistry analysis. Nucleus was stained by DAPI. Each layer of the retina was confirmed via the position of the nucleus, including vitreous, GCL, IPL, INL, OPL, ONL, PR and RPE. Choroid and sclera that wrap around the retina can also be located. (GCL—ganglion cell layer, IPL—inner plexiform layer, INL—inner nuclear layer, OPL—outer plexiform layer, ONL—outer nuclear layer, PR—photoreceptors, RPE—retinal pigment epithelium). The fluorescence signals of MSNs were observed to evaluate the MSN distribution in the posterior segment of eye. One hour after injection, 20 nm MSNs were rapidly crossed through retina and stayed in RPE, choroid and sclera. 30 nm MSNs were observed in all layers of retina, choroid and sclera, 50 nm MSNs were observed in all layers of retina but not in choroid and sclera. One day after injection, most signals of 20 nm MSNs had been clear, most 30 nm MSNs particles distributed in the PR and RPE layer of retina, choroid and sclera, most 50 nm MSNs particles distributed in all layers of retina, choroid and sclera (FIG. 2). Results revealed that MSNs exhibited effective retinal penetration and can modulate the distribution by particle size, MSN with smaller size had higher penetration capability and larger size can retain in layers of retina longer, therefore the distribution and half-life of MSN in the retina can be modulated through particle size. The effect of MSN particle size on penetration capability also have been studied in the rat model and the results were similar to the studies in mice.

Particle Size and Charge Affect Intraocular Distribution and Kinetics (Administration Route: Eye Drop)

Figure 3:
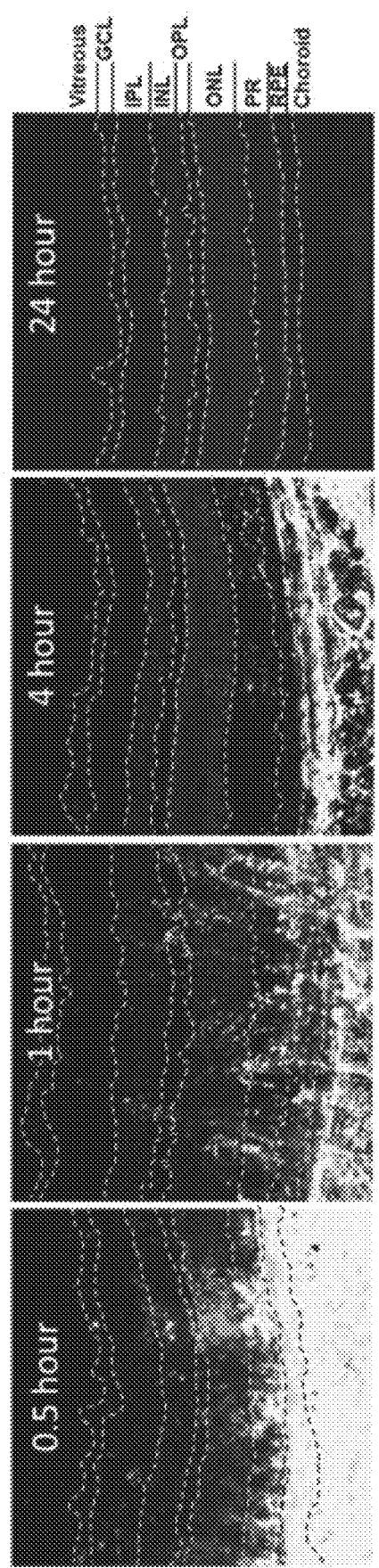
FIG. 3 shows the particles distribution in layers of retina, choroid and sclera at 0.5, 1, 4, 24 hours after treatment of MSN eyedrop formulation.

Fluorescent labeled MSNs with different particle sizes (TEM size: 20 and 30 nm respectively) or different surface charge (negative, neutral, positive) were suspended in PBS and dripped on the surface of mouse eye through eye drop. At different time points (0.5, 1, 4, 24 hours) after eye drop administration, the eyes of the mice were harvested and the frozen section of eyes will be analyzed by immunochemistry analysis. Nucleus was stained by DAPI. Each layer of the retina was confirmed via the position of the nucleus and the fluorescence signals of MSNs were observed to evaluate the MSN distribution in the posterior segment of eye. There are obvious signals of MSN in the PR and RPE layer of retina, choroid and sclera up to 4 hours after eyedrop administration. Most MSN particles were cleared from the eye 24 hours after administration, only a few MSNs were observed in the edge of RPE layer (FIG. 3). Furthermore, small size MSNs with different surface charges (negative, neutral, and positive respectively) still can reach the retina, choroid, and sclera through eyedrop, MSN with neutral surface charge exhibit longer retention time. Results revealed that MSN can effectively reach the posterior segment of the eye through the periocular route and can be retained for hours.

Example 5

Pharmacokinetic of Axitinib @MSN in the Eye Following Eye Drop Administration

Figure 4:
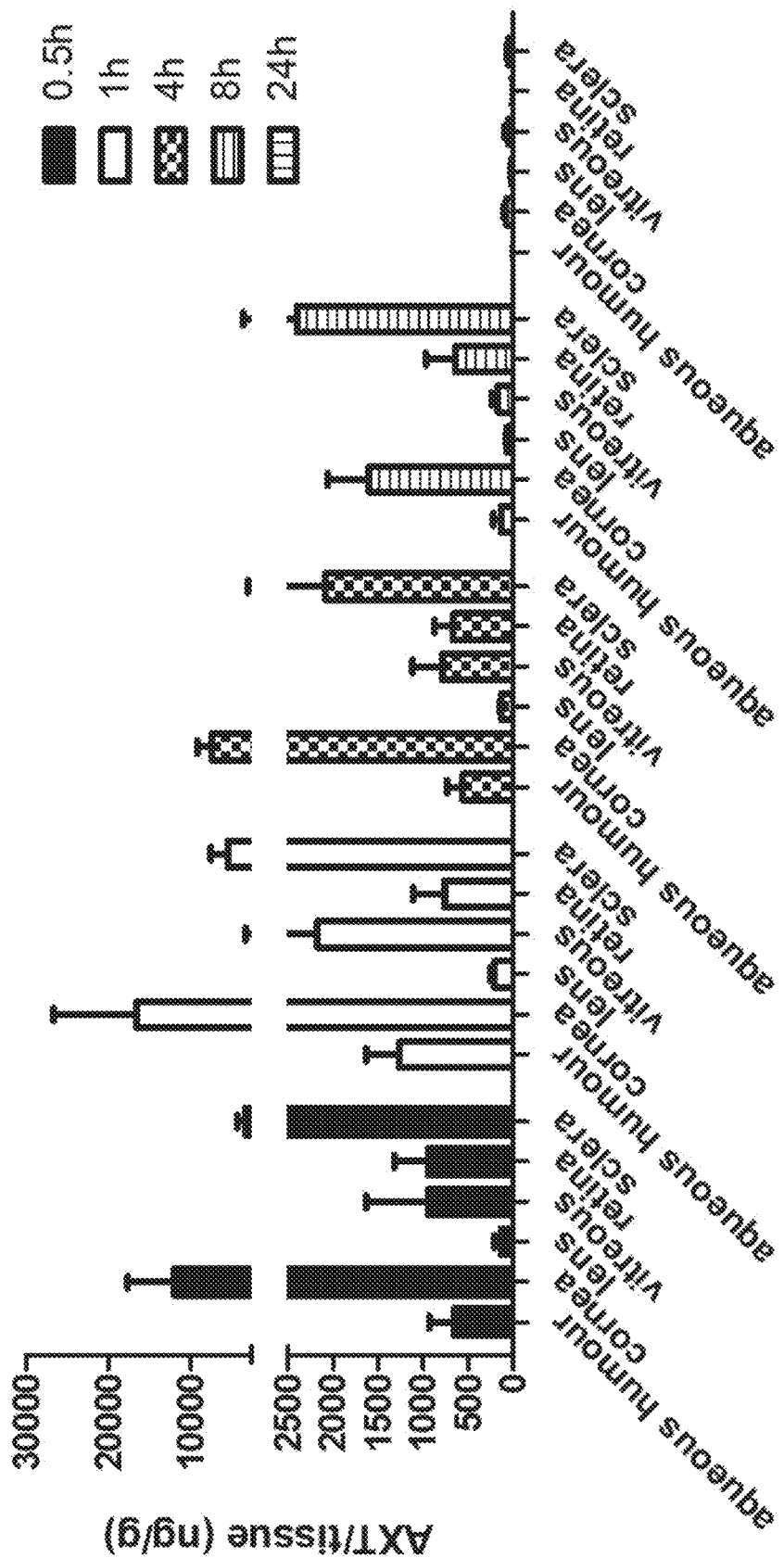
FIG. 4 shows the pharmacokinetics of AXT@MSN in rats eye following eye drop administration.
Figure 5:
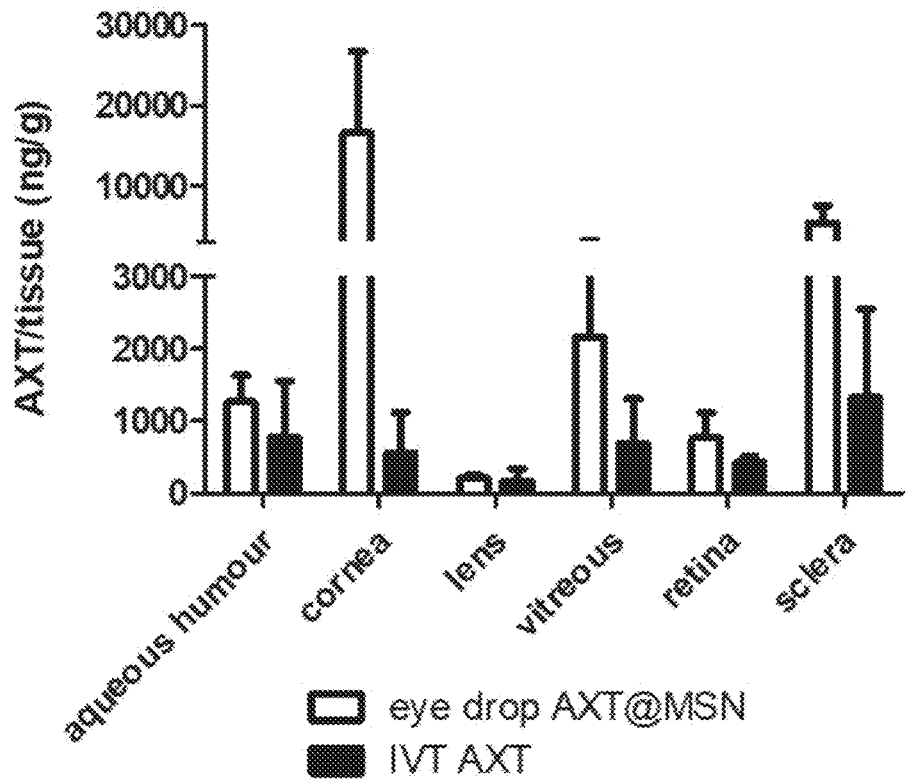
FIG. 5 shows the comparison the concentration of AXT in eye between axitinib alone (IVT) and axitinib@MSN at 1 hour and 4 hour after administration.
Figure 5:
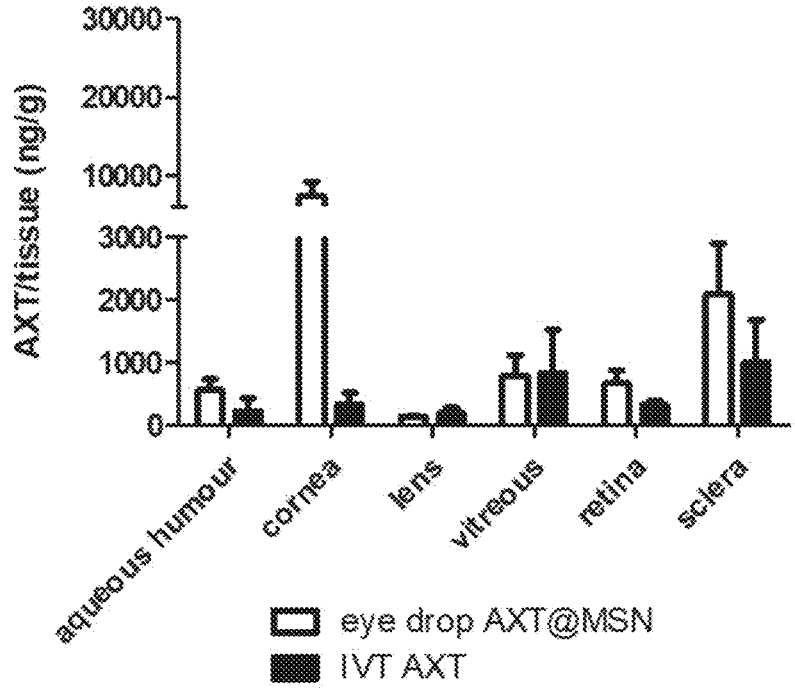

To evaluate the drug delivery efficiency of MSN eyedrop formulation, axitinib loaded MSN (AXT@MSN) was suspended in PBS and dripped one drop on the surface of rat eye through eye drop (10 μL/drop). After 0.5, 1, 4, 8, and 24 hours, eyes were harvested and the aqueous humour, cornea, lens, vitreous, retina, and sclera were isolated for analyze respectively. Tissues were weighted and added with 80% ACN to homogenize by homogenizer with $ZrO_2$ beads, 50% MeOH/50% ACN/0.3% HF (v/v) solution were used for AXT extraction. The extraction solution was centrifuged, the supernatants were collected and dried under a gentle nitrogen stream. Dried supernatants were re-dissolved with solution (80% DMSO/10% acetonitrile/10% $H_2O$) and centrifuged to collect the supernatant. The supernatant was prepared in a solution (35.8% DMSO/2.1% acetonitrile/62.1% $H_2O$) for quantitative analysis by LC-MS/MS. Results revealed that AXT was largely distributed in the cornea and the sclera and was obviously detected in vitreous and retina at 0.5 hours after administration and the AXT concentration in the different parts of eye was decreased over time. AXT@MSN can deliver AXT into the posterior segment of eye (retina, choroid, and sclera) and AXT can be retained in retina for up to 8 hours (FIG. 4). Furthermore, comparison of the concentration of AXT in eye between AXT alone (administration vis intravitreal injection (IVT)) and AXT@MSN (eyedrop) was evaluated. AXT is poorly soluble in water leading to that AXT alone can not be administrated via eyedrop. AXT was dissolved in organic solvent and diluted with PBS to a maximum concentration that did not exhibit aggregation in the solution. The AXT concentration in different parts of eye was detected after 1 hour and 4 hour of administration. Results revealed that the AXT concentration in the posterior segment of eye (retina, choroid and sclara) which treated with AXT@MSN via eye drop was higher than the AXT alone (IVT) treated group (FIG. 5). It means that drugs can be delivered by MSN eyedrop formulation to the posterior segments of eye that offer alternatives of administration route than intravitreal injections.

Efficacy of Axitinib@MSN Eyedrops in a Laser-Induced Mouse Model of Wet-AMD Syndrome

Example 6

Figure 6:
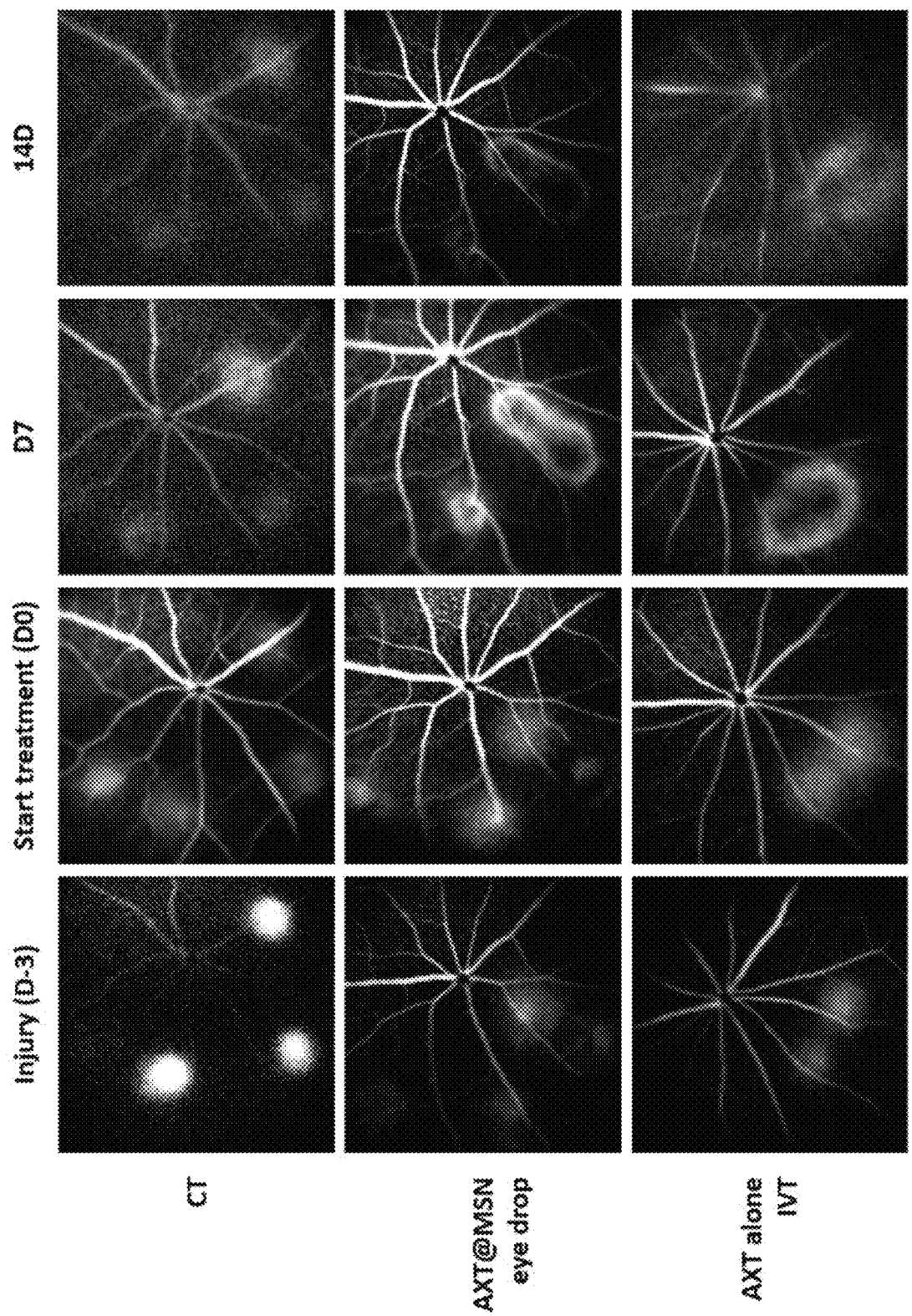
FIG. 6 shows the fundus image (fluorescein angiography) of AXT alone (IVT) and AXT@MSN (eye drop) treated mouse eyes.

The inhibitory efficacy of AXT@MSN on neovascularization was evaluated using a laser-induced mouse model of wet-AMD syndrome. The treatment started 3 days after laser induction. AXT alone or AXT-loaded MSN (AXT@MSN) was suspended in PBS and injected into the eye once a week or instilled on the eye surface twice a day for five days a week. Fundus images were obtained every 2-3 days by optical coherence tomography (OCT) and fluorescein angiography was detected by injecting Fluorescite to examine the leakage from angiogenesis (FIG. 6). Choroidal neovascularization (CNV) is new blood vessels that grow from the choroid underlying the RPE layer of the retina and are accompanied by vascular leakage. The area of dye leakage from CNV lesions can be used to evaluate the level of neovascularization. The area of dye leakage from CNV lesions of AXT@MSN (eyedrop) and AXT alone (intravitreal injection) treated groups obviously decreased compared to the control group, and the leakage area decreased over time. Results revealed that AXT in MSN nanoformulation can be delivered into the posterior segment of eye to achieve effective amount and inhibit neovascularization via eye drop formulation. MSN loaded with therapeutic agents can be used for wet AMD treatment via eye drop formulation.

Example 7

Ocular Toxicity of MSN

The ocular toxicity of MSN was evaluated in mice and rats. MSNs were injected into mouse eyes via intravitreal injection. 1 hour, 1 day and 3 days after nanoparticle injection, mice were observed for morphological changes: (OCT and fundus images), and the retinal structures were examined through frozen tissue sections at different time points. No acute eye irritation/corrosion and no damage to the retina were observed of the eye treated with MSNs. The ocular toxicity of MSN eye drop formulation was evaluated in rats. Rats were applied MSN on the surface of eyes every two-hour intervals four times. The eye irritations/corrosions are evaluated by the Draize eye irritation test and modified OECD405 guideline, the eyes were collected for histopathology study one hour after last administration. No acute eye irritation/corrosion and no significant change of eye tissues were observed of the eye treated with MSNs. Results revealed that MSN is biocompatible for ocular applications.

In summary, small size MSN with specific pore internal surface and outer surface modification have capabilities of loading various active ingredients, delivering drugs across barriers of eye, and offering alternatives of administration route than intravitreal injections, indicating MSN provides an attractive technology to extend the formulation toolbox to the ocular delivery and a method for delivering an agent to posterior segments of an eye, especially delivery via eye drop.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. A method for delivering an agent to posterior segment of an eye comprising administrating a pharmaceutical composition comprising the agent and mesoporous silica nanoparticles to the eye, wherein the agent is loaded by mesoporous silica nanoparticles, and an average hydrodynamic diameter of the mesoporous silica nanoparticles or an average hydrodynamic diameter of the mesoporous silica nanoparticles loaded with the agent is less than 60 nm measured in phosphate buffered saline (PBS) by dynamic light scattering.

2. The method according to claim 1, wherein the agent is a small molecule drug or a biomolecule selected from a polypeptide, an antibody, a fragment of antibody, a fusion protein, a ligand, a biomolecule-binding protein, a functional fragment of protein, an enzyme, or a nucleotide.

3. The method according to claim 1, wherein the agent is difluprednate, loteprednol, dexamethasone, dexamethasone sodium phosphate, fluocinolone acetonide, fluorometholone, triamcinolone, triamcinolone acetonide, rimexolone, prednisolone, medrysone, verteporfin, bevacizumab, ranibizumab, pegaptanib, aflibercept, brolucizumab, faricimab, axitinib, idebenone, azathioprine, methotrexate, mycophenolate mofetil, cyclosporine, tacrolimus, sirolimus, cyclophosphamide, chlorambucil, infliximab, adalimumab, etanercept, or brimonidine.

4. The method according to claim 1, wherein the agent is loaded within pores of the mesoporous silica nanoparticles.

5. The method according to claim 1, which comprises administrating the pharmaceutical composition through topical administration, intravitreal, subretinal, subconjunctival, peribulbar, retrobulbar, intracameral, sub-tenon, posterior juxta scleral, suprachoroidal injection.

6. The method according to claim 1, wherein the pharmaceutical composition is in a form of an eye drop.

7. The method according to claim 1, which is for delivering the agent through cornea, corneal epithelium, Bowman's layer, stroma, Descemet's membrane, corneal endothelium, conjunctiva, blood aqueous barrier, blood retinal barrier, retina, retina vessels, or retinal pigment epithelium or for delivering the agent to layers of retina, choroid or sclera of the eye.

8. The method according to claim 6, wherein an average particle size of mesoporous silica nanoparticles is less than 50 nm measured by transmission electron microscope.

9. A method for treating an ocular disease in a subject in need of such treatment comprising the method according to claim 1.

10. The method according to claim 9, wherein the ocular disease is a posterior segment-related disease.

11. The method according to claim 9, wherein the ocular disease is correlated to abnormal reactive oxygen species level, abnormal apoptosis, abnormal angiogenesis, mitochondrial dysfunctions, inflammation, abnormal protein level or protein misfolding/aggregation/decrease in or complete loss of function.

12. The method according to claim 9, which is for treating a tissue of retina, choroid, sclera, macula, fovea, optic nerve, vitreous humor, iris, cornea, pupil, lens, zonule fibers, or ciliary muscle.

13. The method according to claim 9, which is for treating a cell of a muller cell, photoreceptors, bipolar cell, ganglion cell, horizontal cell, or amacrine cell.

14. The method according to claim 9, wherein the ocular disease is age-related macular degeneration, Leber hereditary optic neuropathy, glaucoma, X-linked juvenile retinoschisis (XLRS), diabetic retinopathy, diabetic macular edema, retinal artery or vein occlusion, uveitis, endophthalmitis, myopic foveoschisis, macular edema, enhanced blue cone syndrome, inflammation following cataract surgery (Irvine-Gass syndrome), retinal detachment, cystoid macular edema, retinal tear, retinal injury, cataract, dry eye, retinitis pigmentosa, retinoblastoma, retinal ischemia, Kearns-Sayre syndrome (KSS), dominant optic atrophy (DOA), orbital inflammatory disease, scleritis, episcleritis, iritis, sarcoidosis, Fuchs' heterochromic iridocyclitis, pemphigoid, ocular toxoplasmosis, ocular graft versus host disease, Stargardt's disease, retinopathy of prematurity (ROP), neovascular glaucoma, and corneal neovascularization secondary to infectious or inflammatory processes.

15. The method according to claim 1, wherein the mesoporous silica nanoparticles have pore internal surface modification with a positively charged molecule or a negatively charged molecule, and the agent is hydrophilic and/or carries positive charge or negative charge.

16. The method according to claim 6, wherein the mesoporous silica nanoparticles have pore internal surface modification with a positively charged molecule or a negatively charged molecule, and the agent is hydrophilic and/or carries positive charge or negative charge.

* * * * *